United States Patent [19]

Tuttle

[11] Patent Number: 4,483,860

[45] Date of Patent: Nov. 20, 1984

[54] HYPERKINETIC CHILD TREATMENT AGENT

[75] Inventor: Ronald R. Tuttle, Plantation, Fla.

[73] Assignee: Key Pharmaceuticals, Inc., Miami, Fla.

[21] Appl. No.: 531,326

[22] Filed: Sep. 12, 1983

[51] Int. Cl.³ .............................................. A61K 31/485
[52] U.S. Cl. ..................................................... 424/260
[58] Field of Search .......................................... 424/260

[56] References Cited

PUBLICATIONS

Chem. Abst. 10th Collective Index, Chem. Substance: Methanediamine–1–Naphthalenol.

Primary Examiner—Stanley J. Friedman
Attorney, Agent, or Firm—Wegner & Bretschneider

[57] ABSTRACT

A method of orally treating a child having a tendency to be overactive to the extent of requiring an external control which comprises orally administering to said child a pharmaceutically effective amount of (−)-17-(cyclopropylmethyl)-4,5-alpha-epoxy-3,14-dihydroxymorpinan-6-one to said patient, whereby the attention span of the child lengthened. An oral sustained release dosage unit containing (−)-17-(cyclopropylmethyl)-4,5-alpha-epoxy-3,14-dihydroxymorpinan-6-one is disclosed also.

4 Claims, No Drawings

HYPERKINETIC CHILD TREATMENT AGENT

BACKGROUND OF INVENTION

The present invention relates to a treating agent for a hyperkinetic child and to a method of treating a hyperkinetic child.

The problems associated with hyperkinetic children are profound. Not only is a hyperkinetic child a distraction to those around him, he is often times his own worst enemy. A major problem with a hyperkinetic child is a very short attention span making learning difficult, if not impossible. The present invention is directed to a treating agent for a hyperkinetic child and a method of treatment that will provide for an acceptable attention span to facilitate learning.

DESCRIPTION OF THE INVENTION

In accordance with a first aspect of the invention there is provided a method of orally treating a child having a tendency to be overactive to the extent of requiring an external control which comprises orally administering to said child a pharmaceutically effective amount of (−)-17-(cyclopropylmethyl)-4,5-alpha-epoxy-3,14-dihydroxymorpinan-6-one, whereby the attention span of the child is lengthened. Preferably, the oral treatment is once or twice daily, although shorter intervals of administration are possible. The dosage is calculated on a basis such that the pharmaceutically acceptable amount is from about 5 to about 75 mg per day based upon a normal child's body weight, which is taken as 30 kg.

Although a parent is usually present at breakfast and dinner so that dosage administration can be monitored at such times, this is not always possible at luncheon; therefor, a sustained release form that permits administration of the medication only at breakfast and dinner is contemplated in a preferred aspect of the invention. Accordingly it is contemplated that there be provided an oral sustained release dosage unit form suitable for treating a child having a tendency to be overactive to the extent of requiring an external control, said oral sustained release dosage unit form permitting a prolonged interval between administration to said child, said oral dosage unit formulation comprising a plurality of granules which together constitute a pharmaceutically effective amount of (−)-17-(cyclopropylmethyl)-4,5-alpha-epoxy-3,14-dihydroxymorpinan-6-one to provide a sustained action, said plurality of granules each comprising a polymeric matrix to permit a substantially even release of (−)-17-(cyclopropylmethyl)-4,5-alpha-epoxy-3,14-dihydroxymorpinan-6-one to permit the necessary sustained release over the prolonged period of time. This oral sustained release dosage unit form may be a tablet compressed of a plurality of granules, optionally including a flavoring agent such as L-aspartyl-L-phenylalanine. Alternatively, the oral sustained release dosage unit form may be a capsule containing a plurality of granules. It is recognized in the scientific community that there are negative side effects with the traditionally used amphetamines. Studies are now being conducted on various opiate receptors. (−)-17-(cyclopropylmethyl)-4,5-alpha-epoxy-3,14-dihydroxymorpinan-6-one provides an excellent form for oral administration, which is not feasible for certain other opioid receptors such as naloxone.

The total daily dosage per child will of course vary dependent upon the weight of the child. The total daily dosage will normally be from about 5 to about 75 mg, and still more preferably about 15 to about 35 mg assuming a normal child weight of 30 kg. In a particularly preferred embodiment, there is contemplated a daily dosage of about 25 mg.

A sustained release dosage unit form is provided for (−)-17-(cyclopropylmethyl)-4,5-alpha-epoxy-3,14-dihydroxymorpinan-6-one to release the active compound over a prolonged period of at least about eight, and preferably at least 12, hours to permit a child to typically take one oral sustained release dosage form before breakfast, for example, when taking orange juice or other breakfast drink, and just before dinner. In a preferred embodiment, the oral dosage unit form is a tablet, but other sustained release forms are also contemplated; for example, capsules or spanules may also be used. As a preferred oral dosage unit form may be mentioned a plurality of granules each of which contains an essentially uniform distribution of the pharmaceutically active ingredient, the (−)-17-(cyclopropylmethyl)-4,5-alpha-epoxy-3,14-dihydroxymorpinan-6-one contained in a sustained release vehicle, which sustained release vehicle releases the (−)-17-(cyclopropylmethyl)-4,5-alpha-epoxy-3,14-dihydroxymorpinan-6-one over a prolonged period of time whereby the possibility of infrequent, preferably not more than twice day, dosing is achieved. As the sustained release vehicle may be mentioned a mixture of cellulosic polymers such as hydroxypropyl methylcellulose typically having a molecular weight of from about 20,000 to about 140,000 and which may be advantageously mixed with polyvinylpyrrolidone having a molecular weight of about 20,000 to about 100,000, and preferably about 40,000. When polyvinylpyrrolidone is used, it is preferably used in an amount of from about 0.2 to about 0.5 parts per unit of cellulosic polymer.

A total dosage of from about 2 to about 25 mg per oral sustained release dosage unit is contemplated. In a preferred embodiment where the oral sustained release dosage unit is to be delivered on a once-per-12 hour basis, the total quantity of (−)-17-(cyclopropylmethyl)-4,5-alpha-epoxy-3,14-dihydroxymorpinan-6-one per dosage unit form is from about 7 to about 20 mg, and still more preferably about 12 mg. It is contemplated that the dosage unit formulation include at least about 200 and preferably at least about 400 of the granules per dosage unit, and not more than about 1500 granules per dosage unit formulation. The use of about 600 such granules is contemplated in a preferred embodiment.

When the oral dosage unit formulation is to be in the form of a tablet, the granules are mixed together with typical tableting excipients, for example, about 1% magnesium stearate. In a further variation of the present invention, there may also be included a minor amount, typically not more than about 3%, of the total weight, of a flavoring agent. This flavoring agent may be based upon a sweetener that is essentially devoid of significant caloric value. In this variation, the flavoring agent is added to the mixture preferably in an amount of about 0.2 to about 1% of the tablet weight. Representative sweeteners without significant caloric value are, for example, saccharine of L-aspartyl-L-phenylalanine.

As an alternative embodiment to the tablet as the oral dosage unit formulation may be mentioned a capsule, which would simply include the necessary plurality of granules that would be released into the gastrointestinal tract upon the dissolution of the capsule.

A rectal suppository is also contemplated as an alternate sustained release vehicle, in which case a wax vehicle is contemplated for the sustained release of the (−)-17-(cyclopropylmethyl)-4,5-alpha-epoxy-3,14-dihydroxymorpinan-6-one over the desired prolonged period of time. While (−)-17-(cyclopropylmethyl)-4,5-alpha-epoxy-3,14-dihydroxymorpinan-6-one has been referred to as the active ingredient of the present invention, it is contemplated that any pharmaceutically acceptable salt form may be used, and it is preferred that the hydrochloride be used in formulations unless otherwise specified. Other forms derived from (−)-17-(cyclopropylmethyl)-4,5-alpha-epoxy-3,14-dihydroxymorpinan-6-one may also be used and are specifically considered to be within the scope of the invention.

The following examples serve to illustrate the invention:

EXAMPLE I

Mixed together are 23 g (−)-17-(cyclopropylmethyl)-4,5-alpha-epoxy-3,14-dihydroxymorpinan-6-one, 140 g polyvinylpyrrolidone (mw 40,000), and 250 gm hydroxypropylmethylcellulose (mw=120,000, Methocel K15M, Dow Chemical). The blend which results from this mixture is granulated with 160 ml deionized water to produce granules which are then dried at a temperature of 50° C. and then ground. The sufficiently small granules which are obtained by passing the mixture of granules through a 14 mesh screen are then lubricated with 5 mg magnesium stearate, and tablets having a total weight of 500 mg are thereafter compressed from this mixture.

EXAMPLE II

By following the procedure set forth in Example I, but adding 4 mg L-aspartyl-L-phenylalanine together with 5 mg of magnesium stearate, there is obtained a sweetened tablet without significant caloric value.

What is claimed is:

1. A method of orally treating a child having a tendency to be overactive to the extent of requiring an external control which comprises orally administering to said child a pharmaceutically effective amount of (−)-17-(cyclopropylmethyl)-4,5-alpha-epoxy-3,14-dihydroxymorpinan-6-one to said child, whereby the attention span of the child is lengthened.

2. The method of claim 1 wherein said periodic oral delivery is at least once per day.

3. The method of claim 2 wherein said periodic oral delivery is at least twice per day.

4. The method of claim 1 wherein said pharmaceutically acceptable amount is from about 5 to 75 mg per day based upon a normal child's body weight.

* * * * *